(12) United States Patent
Dussia

(10) Patent No.: US 7,464,043 B1
(45) Date of Patent: Dec. 9, 2008

(54) COMPUTERIZED METHOD AND SYSTEM FOR OBTAINING, STORING AND ACCESSING MEDICAL RECORDS

(76) Inventor: Evan E. Dussia, 7000 Duck Cove Rd., Tallahassee, FL (US) 32312

( * ) Notice: Subject to any disclaimer, the term of this patent is extended or adjusted under 35 U.S.C. 154(b) by 1598 days.

(21) Appl. No.: 09/616,276

(22) Filed: Jul. 14, 2000

Related U.S. Application Data

(60) Provisional application No. 60/185,577, filed on Feb. 28, 2000.

(51) Int. Cl.
*A61B 5/00* (2006.01)
(52) U.S. Cl. .............. 705/3; 705/2; 600/300; 128/900; 709/202
(58) Field of Classification Search ............ 705/2, 705/3; 600/300; 128/900; 709/202
See application file for complete search history.

(56) References Cited

U.S. PATENT DOCUMENTS

| | | | |
|---|---|---|---|
| 5,772,585 A * | 6/1998 | Lavin et al. ............ | 600/300 |
| 5,867,821 A * | 2/1999 | Ballantyne et al. ....... | 705/2 |
| 5,911,132 A * | 6/1999 | Sloane .................. | 705/3 |
| 5,924,074 A | 7/1999 | Evans | |
| 5,949,875 A * | 9/1999 | Walker et al. ........... | 702/78 |
| 6,206,829 B1 * | 3/2001 | Iliff ................... | 600/300 |
| 6,347,329 B1 * | 2/2002 | Evans .................. | 709/202 |

OTHER PUBLICATIONS

Lan Vision Systems, Inc. Helps Memorial Sloan -Kettering Manage Continum of Patient Care, Despite Disaster PR Newswire; New York, Aug. 27, 1998;pp. 1-2.*

\* cited by examiner

*Primary Examiner*—Vanel Frenel
(74) *Attorney, Agent, or Firm*—James H. Beusse; Beusse Wolter Sanks Mora & Maire, P.A.

(57) ABSTRACT

Computerized method and system for managing respective health records of a plurality of patients are provided. The method allows for uploading a progress note of a respective patient. The progress note includes data relative to an encounter between a respective physician and the respective patient. The method further allows for identifying on the progress note respective parameters selectable by the respective physician. A storing step allows for storing the progress note with the identified parameters in a database accessible to a plurality of authorized users. A populating step allows for populating the database with respective progress notes resulting from further encounters between the respective patient and any respective physician so as to create a historical set of progress notes for that respective patient.

19 Claims, 5 Drawing Sheets

COMPUTERIZED METHOD AND SYSTEM FOR OBTAINING, STORING AND ACCESSING MEDICAL RECORDS

This application claims the benefit of U.S. provisional application No. 60/185,577 filed on Feb. 28, 2000.

A portion of the disclosure of this patent document includes material which is subject to copyright protection. The copyright owner has no objection to the facsimile reproduction by anyone of the patent document or the patent disclosure, as it appears in the Patent and Trademark Office Patent File or records, but otherwise reserves all copyrights rights whatsoever.

BACKGROUND OF THE INVENTION

The present invention relates to a system and method for managing medical patient records and, more particularly, to a computerized system and method which provides for the capture, storage, processing, communication, security and presentation of non-redundant patient health information over an Internet connection.

It is believed that prior to the present invention nearly all communication between doctors' offices regarding patient records has been by paper or by telephone. This is also true of communications between doctors' offices and insurers, HMOs, MCOs, hospitals, and a pharmacies. Known medical data systems have suffered from undesirable data cluttering due to attempting to be all encompassing and have been generally designed around information gathering parameters, rather than providing narrowly focused and unobtrusive management of the patient records. It is further believed that no single system has gained wide acceptance for medical records management in the office environment, and none has been designed for data sharing among multiple users.

In view of the above-described issues, it would be desirable to provide a system that is user-friendly, and provides straightforward inquiry screens which display essential patient information from the doctor's viewpoint, such as diagnosis and treatment plans. It would be further desirable to enable the user "to see" into the thought process of the treating physician. If more detailed information is desired, the viewer may just "point and click" to see the entire text of the physician's progress (or encounter) notes while avoiding the potential for data cluttering due to useful but not necessarily essential data, such as lab tests, scans, and X-rays images. It is also desirable to provide a system and method that would:

Assist specialist practitioners to whom a patient has been referred, by eliminating most requests for file data from referring physicians, and removing guesswork and office time involved in obtaining a complete list of medications which the patient may be using.

Make after hours and emergency hospital visits more risk free because of the availability of patient information on a permanent round-the-clock basis. At present, records are generally unavailable when the physicians' offices are closed. Additionally, records are fragmented and scattered among all practitioners with whom the patient is associated. Even in those rare instances where the patient in the emergency room is knowledgeable concerning his own medical history and drug therapies, if he or she is in shock, in great pain, or unconscious, it is currently difficult for the attending physician to quickly obtain patient medical data.

Enable druggists to avoid drug interactions and allergic reactions in filing prescriptions. Since patients may obtain their prescription medications from more than one location, then it is currently very difficult, if not impossible, for pharmacists to fulfill their potential in helping patients avoid adverse drug interactions.

Enable health insurers, such as HMOs and managed care companies, to perform the required quality assurance inspections and utilization reviews off-site with the click of a button at a fraction of the current costs. Both of these functions are currently performed by inspectors and auditors who actually go to the practitioner's office and have his/her staff pull files. The individual files are then reviewed and certain documents (i.e., the progress notes, problem list, treatment plan and drug list) may be copied by the doctor's staff. Then the files need to be returned to their proper place and annotated. This process is expensive for both companies and for the physicians, which of course translates into higher costs for patients.

SUMMARY OF THE INVENTION

Generally speaking, the present invention in one aspect thereof fulfills the foregoing needs by providing a medical health record storage and retrieval system comprising an interface module configurable to extract a patient's medical diagnosis and treatment from respective progress notes of a physician. A storage module is configured to store the extracted diagnosis and treatment in a logically connected database. A server is configured to allow access to the stored database by authorized users, and a processor module is configured to track users accessing the database and to bill the accessing users for each access of the database.

The present invention further fulfills the foregoing needs by providing in another aspect thereof a computerized method for managing respective health records of a plurality of patients. The method allows for uploading a progress note of a respective patient. The progress note comprises data relative to an encounter between a respective physician and the respective patient. The method further allows for identifying on the progress note respective parameters selectable by the respective physician. A storing step allows for storing the progress note with the identified parameters in a database accessible to a plurality of authorized users. A populating step allows for populating the database with respective progress notes resulting from further encounters between the respective patient and any respective physician so as to create a historical set of progress notes for that respective patient.

In yet another aspect thereof, the present invention further provides a computer-readable medium encoded with computer program code for managing respective health records of a plurality of patients. The program code causes a computer to execute a method comprising:

uploading a progress note of a respective patient, said progress note comprising data relative to an encounter between a respective physician and the respective patient;

identifying on said progress note respective parameters selectable by the respective physician;

storing said progress note with said identified parameters in a database accessible to a plurality of authorized users; and populating said database with respective progress notes resulting from further encounters between the respective patient and any respective physician so as to create a historical set of progress notes for that respective patient, the set of historical progress notes being interconnectable based on one or more logic operators.

Figure 1:
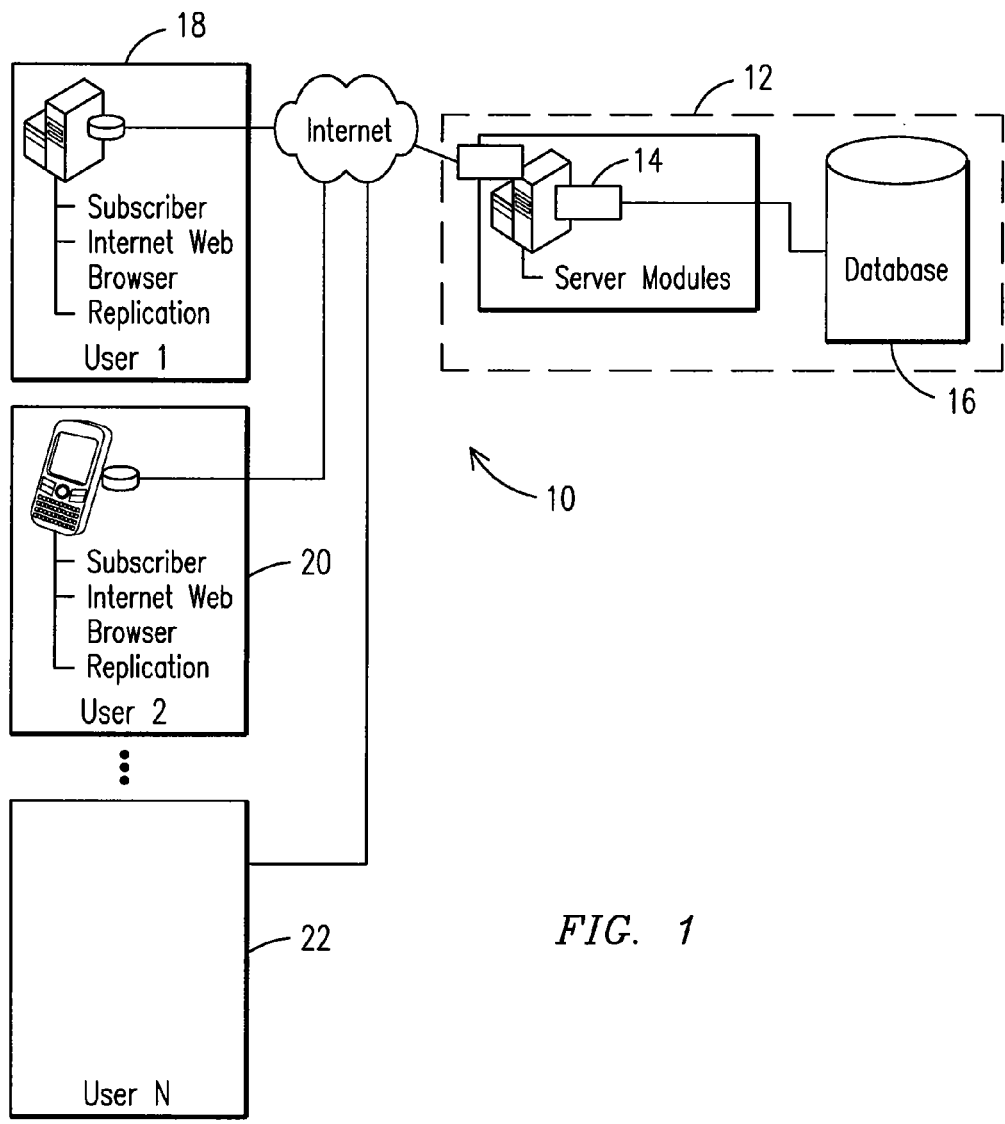
FIG. 1 illustrates an exemplary block diagram of a system for managing medical records that embodies one aspect of the present invention.

Before any embodiment of the invention is explained in detail, it is to be understood that the invention is not limited in its application to the details of construction and the arrangements of components set forth in the following description or illustrated in the drawings. The invention is capable of other embodiments and of being practiced or being carried out in various ways. Also, it is to be understood that the phraseology and terminology used herein is for the purpose of description and should not be regarded as limiting.

DETAILED DESCRIPTION OF THE INVENTION

Definitions, Acronyms and Abbreviations

Physician: A user representing a physician or physician's office, who does not necessarily has to be a physician but has access to the system.

Pharmacy: A user representing a pharmacy or a pharmacist, having access to the system.

Hospital: A user representing a hospital, having access to the system.

Insurance Company: A user representing an insurance company, having access to the system.

Pharmaceutical Company: A user representing a pharmaceutical company, having access to the system.

Transcription Service/Transcriber: Transcription services are users of the system responsible for entering progress notes into the system.

User: Anyone with an account allowing them access to the system.

GUI: Graphical User Interface. A graphics-based interface using icons, pull down menus, and other computer peripherals, e.g., a mouse, that enables the user to interact with the system.

HTML: HyperText Markup Language. The scripting language used to build web pages.

ASP: Active Server Pages. A technique for using programming and logic to dynamically process web pages on a server, as they are requested from a client browser. ASP pages will be able to interface with COM objects running in a transaction server, allowing the application access to the data through a business layer contained in a COM object.

COM: Component Object Model. A model for developing architectural components that allows for configuring a component so that other applications and programs may interface with it.

IIS: Internet Information Server. A Web server available from Microsoft that allows client browsers to request web pages and serves those pages to the browsers. The user interface to the application will comprise web pages being served and maintained by IIS.

Transaction Server: A server, also available from Microsoft, that manages the COM objects. A middle-tier business logic of the application will be contained within a COM component running within the transaction server.

MS SQL: Microsoft database server based on structured query language. SQL will store the data tables, views, triggers and stored procedures that process the data. SQL is accessed from the application through the COM object running on Transaction Server.

Progress Note: A progress note is a description of the physician's meeting with a patient. The information contained within a progress note comprises the time and date of the note, the physician, the patient, and a description of the reason for the visit. This description will generally include the diagnosis or diagnoses and any necessary prescription(s).

Diagnosis: A physician's diagnosis.

Prescription: A prescription prescribed for a diagnosis.

Owner: The physician who is responsible for entering the patient into the system. This will not necessarily be the patient's primary physician.

Parent: When a new physician is referred to the system and becomes a participant or subscriber, the physician who referred the new physician is the new physician's parent.

CSS: Cascading Style Sheets. CSS 1.0 is a specification for the authoring of style sheets within an HTML document. The style sheets assist in code reuse and in giving web pages a similar look and feel across an application.

SSL: Secure Socket Layer. A technique for sending encrypted data across public data lines.

Billing/Maintenance Information: This term labels an entity's address and contact information. This is to distinguish between patients and users of the system. Patient's information will be referred to as demographic information and will include address and contact information, as well as insurance information, if available. Other system entities' address and contact information will be referred to as Billing/Maintenance Information.

Insert: Insert permission allows the user the ability to add records to the system. If the user does not have insert permission for an entity type, they will not be able add new records of that entity type.

Update: Update permission allows the user the ability to update existing records in the system. If the user does not have update permission for an entity type, they will not be able update records of that entity type.

Overview

The present invention in one aspect thereof permits universal and timely access to health information for approved care givers and other authorized users 24 hours a day, seven days a week using a web-enabled system 10, as shown in FIG. 1. The system allows on-line access to a patient's health history by approved caregivers. The system uses the physician's work product in the form of dictated progress notes as the foundation document for extracting a patient's medical history. An extraction module operates in a free text environment of the dictated progress note to extract the problem or diagnosis and the treatment or drug specified by the physician and places that information on a logically connected chart, such as a Web page. The connection may be based using one or more logic operators that may be indicative of various criteria for conducting analysis in a set of historical progress notes, such as chronological, pathological, pharmacological, and other criteria. Persons having authorized access to the system may be able to access the actual source document in the form of the progress note through the chart screen. As suggested above, the progress notes may be logically connected within a respective pathology and treatment therefor so that the physician or third party payor, e.g., health insurance carrier, can track a particular problem over its course in the life of a particular patient, or over any chosen chronological period. The progress notes can be transmitted into the system directly by the transcriber or transcription service thereby obviating the necessity of training and staffing the medical office for data input.

In one exemplary embodiment, data in the system is remotely accessible over the Internet using a respective computer using a web browser or by a cell phone with Internet access. Further, some phones with automated voice read back or handheld personal communication devices may be utilized to access information from the data storage device.

The medical records are organized or logically connected in a manner that facilitates easy usage by a remote caregiver such as an emergency room physician. The input of the medical data and the type of medical information utilized is selected to convey a snapshot of respective encounters between physician and patient to quickly alert the remote caregiver of any particular nuances in treatment of a patient, such as medical or drug sensitivity or the use of secondary drugs that may interact with primary drugs being taken by the patient. The system has appropriately restricted access and sufficient data encryption to prevent unauthorized persons from obtaining information from the medical database.

As shown in FIG. 1, system 10 may comprise a Web-based, distributed application that may be configured through a graphical user interface for uploading, or downloading, or both, one or more Web pages from a Web site 12, such as may be operated by the Assignee of the present invention. A server 14 comprises respective modules for managing business rules and data access to a database 16, such as a centralized database, operable to store patient and physician information. As suggested above, appropriate security measures, such as data encryption, and passwords are provided in server 14 to grant access to database 16 only to those users with pre-approved rights.

A plurality of participating or subscribing users, e.g., users 18, 20 and 22, will be able to communicate with server 14 via any suitable communications network, such as the Internet. Thus, users such as physicians, hospitals, pharmacies, ambulance services, emergency medical services, insurance companies, etc. will be able to query database 16 through server 14 from any device connected to the Internet that supports a suitable Web browser. In one advantage of the system of the present invention, due to its straightforward user interface, it is believed that users should be able to learn to navigate through the system after spending no longer than a few minutes. Users connecting to the web site will be asked to log on to gain access to the system. If they successfully log on, they will be able to query the system for information. Below are some examples of some of the users that will benefit from the system of the present invention. It will be appreciated, however, that the present invention is not limited to such users being that any provider of medical services, or provider of services related to the health care industry will also benefit from the present invention.

Physicians

Physicians will primarily use the system to access patient records. They will be able to view past progress notes and validate newly transcribed progress notes. Physicians accessing the system will be able to search for patients, patient's past diagnoses and patient's past prescriptions. Physicians will also be able to view progress notes from patient visits to themselves as well as other physicians. Physicians will also be able to update their own information, their new patients information and update existing patient information, including patient insurance information.

Pharmacies

Pharmacies will be able to search for patients and view a patient's diagnosis and prescription history. They will also be able to update prescription information such as the date the prescription was filled. Pharmacies will also be able to view and update patient insurance information. Pharmacies will maintain their own billing/maintenance information.

Hospitals

Hospitals will generally use the system to search for patients. They will have the ability to view patient diagnosis and prescription history, as well as patient demographic information. Hospitals will also maintain their own billing/maintenance information.

Insurance Companies

By way of example, Insurance Companies may use the system to monitor progress notes of client patients. They will be able to search for physicians and view physician's diagnosis and prescription histories as well as the originating progress notes. Insurance Companies may use the system for multiple purposes, such as utilization review, quality assurance, grievance resolution, and including tracking of particular problems that may develop over the course of a long term condition. Insurance Companies will also maintain their billing/maintenance information.

Pharmaceutical Companies

Pharmaceutical Companies may use the system not necessarily to monitor prescription and diagnosis information of individuals but to have the capability of receiving composite reports analyzing what drugs are being collectively prescribed and how frequently. Thus, it is contemplated that Pharmaceutical Companies may not be granted access to any medical records of individuals. However, it is contemplated that Pharmaceutical Companies will benefit from gaining access to such composite reports. They will also maintain their billing/maintenance information.

Transcription Services

Transcription services will use the system to enter Physicians' progress notes. They will also be responsible for entering their maintenance information.

It will be appreciated that in order to provide maximum benefits, it is desirable for patient information to be accurate and up-to-date. As suggested above, the data will be centrally located and data storage may be executed at predefined time intervals, such as daily and even hourly. It will be further appreciated that as the size of the data managed by the system of the present invention grows, so will the need for broader bandwidth and greater system resources on the database servers. It will be recognized, however, that the techniques of present invention may be adaptable to advancing technologies and is not limited to presently available technology.

Those of ordinary skill in the art will recognize that various uploading techniques may be used for updating the database with new patient information. However, regardless of the specific technique used, the updating should be accomplished in such a way as to minimize the time and effort by physicians, while getting the data into the system in a timely manner. Such uploading techniques may be used for entering other entity information, such as insurance companies, hospitals, pharmacies and pharmaceutical companies. It is envisioned that maintenance of this third party data will be done primarily by the entities themselves. Patient data, however, will be preferably maintained by physicians. Patient insurance information will also be preferably maintained by the patient's physician.

Exemplary Techniques for Updating Data

It is presently envisioned that in one exemplary embodiment there may be at least two different techniques for loading data from the transcription service into the database. One technique will be for the transcribers to enter the transcription on the Web site. One or more web pages will be provided for transcribers to enter information directly into the system. This will allow the data to be immediately available for a physician's review. An alternate technique may be to provide the transcription services with a suitable word processing template, such as a MS Word or a Corel Word Perfect template. The template will have predefined fields for capturing progress note and patient data. Documents based on this template can be e-mailed to an e-mail address that is part of the Web site. A parsing module would be provided to parse the attachment and update the database with the progress note. As further advances in voice recognition occur, it is further envisioned that a physician could dictate using a device with voice-recognition capabilities and automatically generate an electronic file ready to be loaded into the database.

Ability to Enter and Search Progress Notes

The system is configured to allow respective transcribers to insert new progress notes from the transcription service. The physician who originally submitted the progress note for transcription will solely be allowed to review and validate the progress note. Once the physician has validated the progress note, that note is available for viewing only, to all users with the appropriate permissions. As further described below, these permissions are assigned to each user and affect each user's access to various system features.

Ability to Extract Prescriptions and Diagnoses from Progress Note

Figure 2:
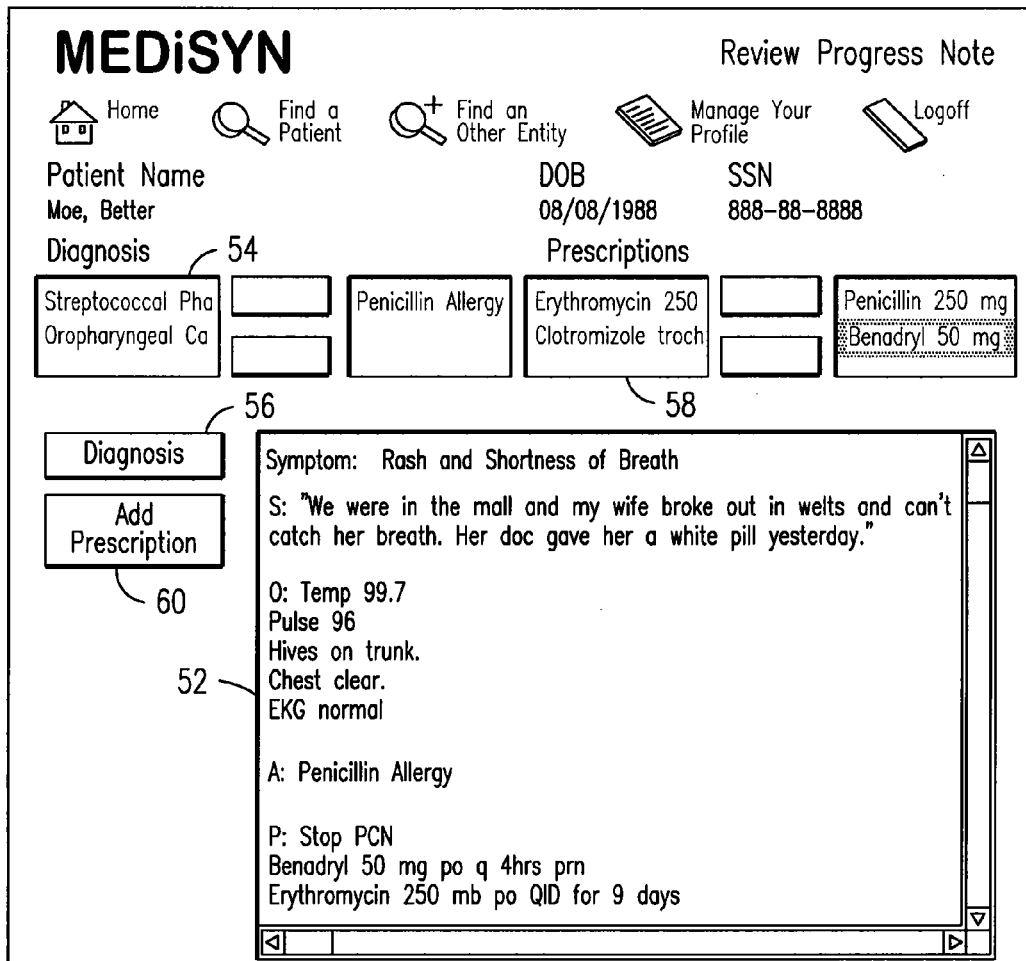
FIG. 2 illustrates an exemplary Web page comprising a progress report based on a respective encounter between a patient and physician including respective diagnosis and prescription data extracted by that physician.

FIG. 2 illustrates a representation of a Web page 50 comprising an exemplary progress note 52. When the submitting physician reviews the progress note, he or she will identify on the progress note respective parameters selectable by that physician. One example of such parameters selectable by the physician may include a respective diagnoses from the progress note. The respective identified diagnosis may be added by the owner physician to a diagnosis list 54 by clicking on an icon 56 titled "Add Diagnosis". Another example of parameters selectable by the physician may include a respective prescription selected by the physician from the progress note. The respective identified prescriptions may then be added to a list of prescriptions 58 by clicking on an icon 60 titled "Add Diagnosis". If a diagnosis or prescription referenced in the progress note text also exists in the diagnosis or prescription list, the referenced item will be added to the diagnosis list or prescription list for that progress note. Each physician will have a respective list of diagnoses. The physician's progress note will generally comprise a subset of this list. As shown in FIG. 2, progress note 52 also identifies the patient with an identifier, e.g., social security number or other suitable identifier, thus associating respective diagnoses with a respective patient. Any given physician will generally have one or more patients and respective patients of a given physician will have one or more progress notes and in turn each respective progress note will have one or more associated diagnoses. Similarly, each respective progress note will have zero or more associated prescriptions. Each of these diagnoses, or prescriptions, or both, can be related to the physician and the patient for searching. Further, each prescription record can be expanded to reference a pharmacy, a start date and an end date for the prescription. The system can thus determine at what pharmacy and on what date a prescription was filled for a given patient under a given physician's care, provided that all three users are enrolled in the system.

Figure 3:
FIG. 3 illustrates an exemplary Web page comprising historical data of diagnosis and prescriptions based on respective progress reports such as shown in FIG. 3.

As shown in FIG. 3, database 16 may be populated with respective progress notes resulting from further encounters between the respective patient and any respective physician treating the patient so as to create a searchable historical set of progress notes for that respective patient. As suggested above, the set of historical notes is logically interconnectable based on one or more logic operators. As shown in FIG. 3, a list of diagnosis including a respective set of hyperlinks 72 each indicative of a respective diagnosis date is provided to enable a respective user to download and review the respective progress note associated with any given diagnosis date. Similarly, a set of hyperlinks 74 may be listed in a desired chronological order to enable the user to monitor progress of a given pathological condition in the patient. FIG. 3 further shows a list of prescriptions including a respective set of hyperlinks 76 each indicative of a respective prescription date that allows the user for logically connecting respective progress notes and prescription dates.

Ability to Search Progress Notes by Diagnosis

As suggested above, physician and users, such as insurance companies, will have the ability to search for progress notes that discussed a specific diagnosis. The user will be presented with a list of diagnoses for a given patient. That list will name the diagnosis, the date of the first occurrence and the date of the most recent occurrence. Selecting one of these items will take the user to a read-only display of the progress note. Here, the user will have the ability to scroll through the progress notes pertaining to this diagnosis.

Ability to Search Progress Notes by Prescription

Similarly, such users will have the ability to search for progress notes that mention a specific prescription. The user will be presented with a list of prescriptions for a given patient. That list will name the diagnosis, the date of the first occurrence and the date of the most recent occurrence. Selecting one of these items will take the user to a read-only display of the progress note. Here, the user will have the ability to scroll through the progress notes pertaining to this prescription.

Ability to Search for Patients

Users will have the ability to search for a patient by the patient's social security number, date of birth, last name and first name. Any combination of these criteria may be used to search for a patient. If only the date of birth field is populated, the search results will contain all patients with that date of birth. If date of birth and last name are populated, then the search results will contain all patients with the date of birth the user entered, having the last name the user entered. If no patients meet the search criteria, a message will display to the user to let them know that no such patient exists and they may want to broaden their search requirements. If multiple patients meet the search criteria, a table will display with each row in the table corresponding to a different patient. The columns will be First Name, Last Name, Social Security Number and Date of Birth.

An example of a table comprising searchable parameters in connection with patient identification is listed in Table 1 below:

TABLE 1

| First Name | Last Name | Social Security Number | Date of Birth |
|---|---|---|---|
| John | Doe | 123121234 | Jan. 1, 1950 |
| Juan | Don | OC0000017 | Mar. 15, 1947 |

It will be appreciated that patients who are not citizens of the United States may not have an assigned social security number. Thus, a module may be provided for tracking patients who are not United States citizens. For example, an alphabetical character may be inserted into the SSN as an indicator that the patient is not a citizen of the US and in that case the search may be conducted by name and date of birth.

Ability to Search Physicians and other Users

Users will have the ability to search for physicians either by name or location, or both. Searching by name will return all physicians in the system where the text entered in the search matches text the physician's name. Searching by location may be broken down by city and postal code. Either field may be used. For example, if both fields contain text, then physicians in the system having an address where the city matches text entered in the city field and a postal code matching text entered in the postal code field, will be returned. Users will further have the ability as described above to search for other users, such as pharmacies, hospitals, insurance companies, transcription services either by name or location, or both.

Ability to Add and Update Patient Demographic Information

In one exemplary embodiment of the system of the present invention, physicians and hospitals will have the ability to modify patient demographic data. The purpose of this functionality is to allow physician's offices and hospitals to have the latest patient demographic information. This information is to include the patient's name, social security number, date of birth, and any other useful contact information. By way of example, contact information may include the patient's address or addresses and their phone number(s) and email addresses, if available. In addition to the standard contact information, the patient's insurance information may also be tracked. Since a given patient may have multiple insurance companies, the system can support the addition and removal of multiple insurance companies for patients. There may also be provided additional fields to enter new insurance companies and make any appropriate changes to insurance company information for those that are already in the system.

Ability to Add and Update Hospital Information and other Users

In one exemplary embodiment of the system of the present invention, physicians or hospitals users can add hospitals into the system. When a physician adds a hospital to the system they do not necessarily create a user for that hospital. Physicians and pharmacies can enter hospital billing/maintenance data, as well as the hospitals. Further, insurance companies can be similarly added by physicians when creating new patient or updating existing patient's information. Similarly, pharmacies can be added by physicians when creating new patient or updating existing patient's prescription.

Validate Progress Note

When a physician logs into the system, they will be presented a list of hyperlinks to all progress notes containing their respective UPIN identifier that have not been validated. When the physician clicks a respective hyperlink, they will be taken to a Web page displaying an editable version of the progress note. The physician will have the ability to update any information contained within the progress note. In addition, the physician will be able to select text from within the progress note and add this text to the diagnosis list or the prescription list. These lists will be populated with the existing diagnoses and prescriptions for the physician. If text within the progress note text matches text in the diagnosis or prescription lists, that text will become selected in the list. This is an indication that the diagnosis or prescription is associated with the progress note. Once the physician submits this progress note, it is available to any other entities with proper permission, to view.

Entering/Updating Billing/Maintenance Information

Users will have access to a page where they can enter their address and contact information. This page will allow users with proper permission to edit their information and other users to view it.

Security and Record Access

It should be apparent that security is important in this type of system due to the sensitivity of patient data. The security for this system will comprise multiple levels. The system will use SSL (Secure Socket Layer) 128 bit encryption. This will ensure that data going between the clients and the web server is encrypted. It is believed that such encryption should prevent hackers from intercepting packets and getting sensitive information. Each Physician, Pharmacy, hospital and pharmaceutical company in the system, will have a user account to gain access. By way of example, the account may comprise a user name, password and entity type; i.e. Physician, hospital, Pharmacy, etc. The user name may require a minimum number of characters, e.g., at least six characters long and may not include the <space> character. Similarly, the password may be at least six characters long and may be case sensitive. The password may be chosen to contain at least one lower and one upper case letter and at least one numeric character. A log of system access attempts may be maintained. This log will consist of user name, password, IP address and date time stamp. This log can be used to determine if there have been unauthorized attempts and if so, where they originated. Tables 2-7 below illustrate exemplary access rights for typical entities that may access the system. An X in the field indicates that the entity has privileges for that task.

TABLE 2

| | Physician: | | | |
|---|---|---|---|---|
| | Search | View | Insert | Update |
| Diagnosis | X | X | X | X |
| Prescription | X | X | X | X |
| Progress Note | X | X | X | X |
| Entity Maintenance | | | | |
| Patient Demographics | X | X | X | X |
| Physician | X | X | X | X |
| Pharmacy | X | X | | |
| Hospital | X | X | | |
| Insurance Company | X | X | X | X |
| Pharmaceutical Company | x | | | |
| Transcription Service | X | X | X | X |

TABLE 3

Pharmacy:

| | Search | View | Insert | Update |
|---|---|---|---|---|
| Diagnosis | X | X | | |
| Prescription | X | X | | |
| Progress Note | | | | |
| Entity Maintenance | | | | |
| Patient Demographics | | X | | X |
| Physician | | X | | |
| Pharmacy | X | X | X | X |
| Hospital | | | | |
| Insurance Company | | X | | |
| Pharmaceutical Company | | | | |
| Transcription Service | | | | |

TABLE 4

Hospital:

| | Search | View | Insert | Update |
|---|---|---|---|---|
| Diagnosis | X | X | | |
| Prescription | X | X | | |
| Progress Note | | | | |
| Entity Maintenance | | | | |
| Patient Demographics | X | X | | X |
| Physician | | X | | |
| Pharmacy | | | | |
| Hospital | X | X | X | X |
| Insurance Company | | X | X | X |
| Pharmaceutical Company | | | | |
| Transcription Service | | | | |

TABLE 5

Insurance Company:

| | Search | View | Insert | Update |
|---|---|---|---|---|
| Diagnosis | X | X | | |
| Prescription | X | X | | |
| Progress Note | X | X | | |
| Entity Maintenance | | | | |
| Patient Demographics | X | X | | |
| Physician | X | X | | |
| Pharmacy | X | X | | |
| Hospital | X | X | | |
| Insurance Company | X | X | X | X |
| Pharmaceutical Company | | | | |
| Transcription Service | | | | |

TABLE 6

Pharmaceutical Company:

| | Search | View | Insert | Update |
|---|---|---|---|---|
| Diagnosis | | | | |
| Prescription | | | | |
| Progress Note | | | | |
| Entity Maintenance | | | | |
| Patient Demographics | | | | |
| Physician | | | | |
| Pharmacy | | | | |
| Hospital | | | | |
| Insurance Company | | | | |
| Pharmaceutical Company | | | X | X |
| Transcription Service | | | | |

TABLE 7

Transcription Service:

| | Search | View | Insert | Update |
|---|---|---|---|---|
| Diagnosis | | | | |
| Prescription | | | | |
| Progress Note | | | | |
| Entity Maintenance | | | | |
| Patient Demographics | | | | |
| Physician | | | | |
| Pharmacy | | | | |
| Hospital | | | | |
| Insurance Company | | | | |
| Pharmaceutical Company | | | | |
| Transcription Service | | | X | X |

Tracking/Billing Module

The system of the present invention includes a module for tracking system usage as a function of entity. As patients are added into the system, each patient will include a primary physician who is a participant in the services provided by the assignee of the present invention. When a user or entity that is not a patient's primary physician accesses that patient's records, that entity may be charged a predefined access fee. The participant who is the patient's primary physician may receive a predefined percentage of the access fee. If the participant was referred to the system by another physician, that referrer may also receive a predefined percentage of the access fee. When an attempt is made to access a record, the tracking module will first determine whether the entity has permission to view the record. If the entity does not have permission, the entity is then compared to the record's owner. If they are the same, no accounting transaction is registered. If they are different, however, the entity accessing the record is a charged a predefined fee in accordance with a predefined entity type billing schedule stored in memory. The owner of the record would then receive a payment record of a predefined percentage of the access charge. The tracking module would then check for respective parents of the owner. If the parent has an owner, that owner level is checked, and they would receive a payment record based on a predefined billing schedule. Then the tracking module would check for parents of the parent and continue with any further iterations until there is no parent record for the present parent.

Figure 4A:
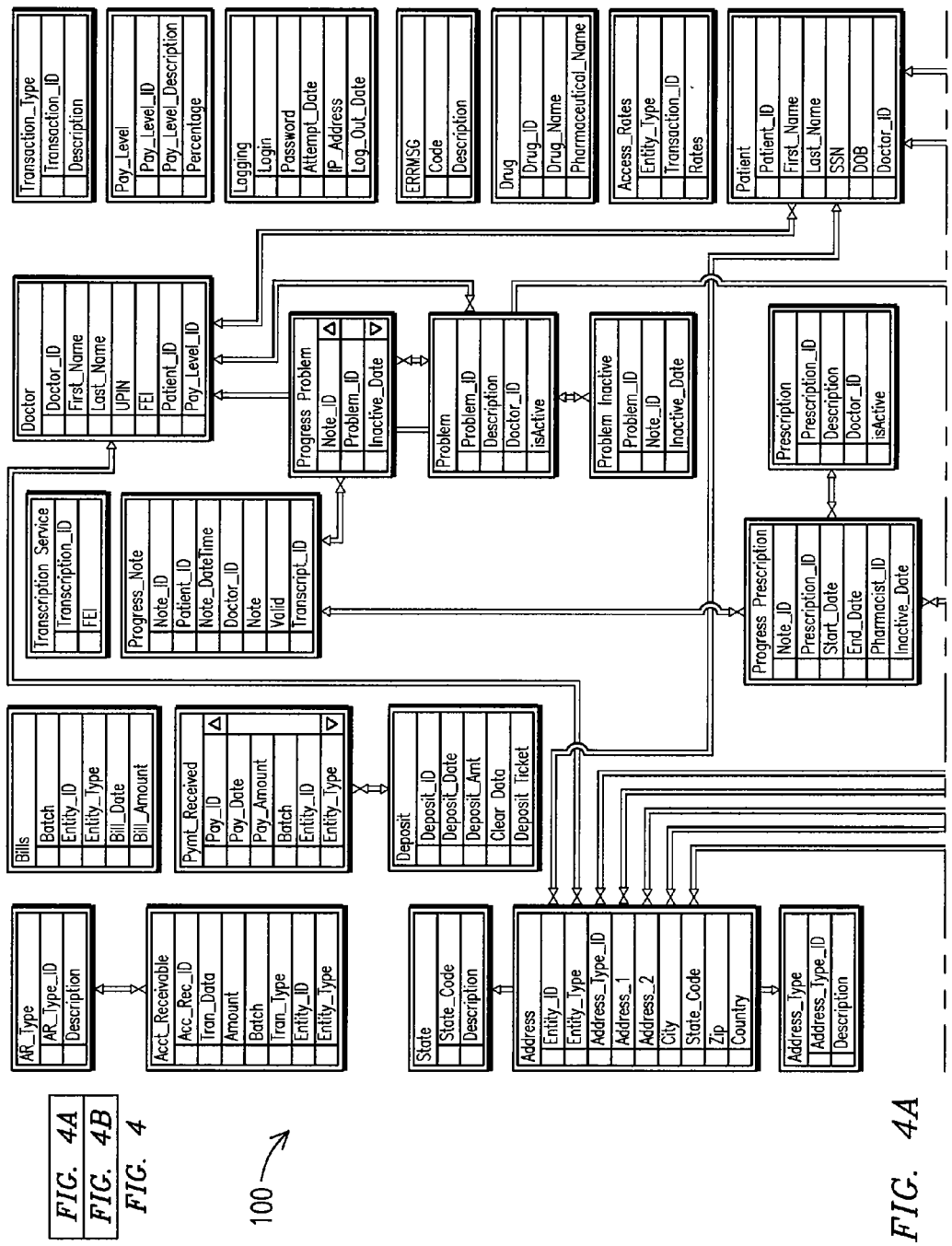
FIG. 4 illustrates an exemplary layout of a data structure including respective data fields for managing medical records.
Figure 4B:
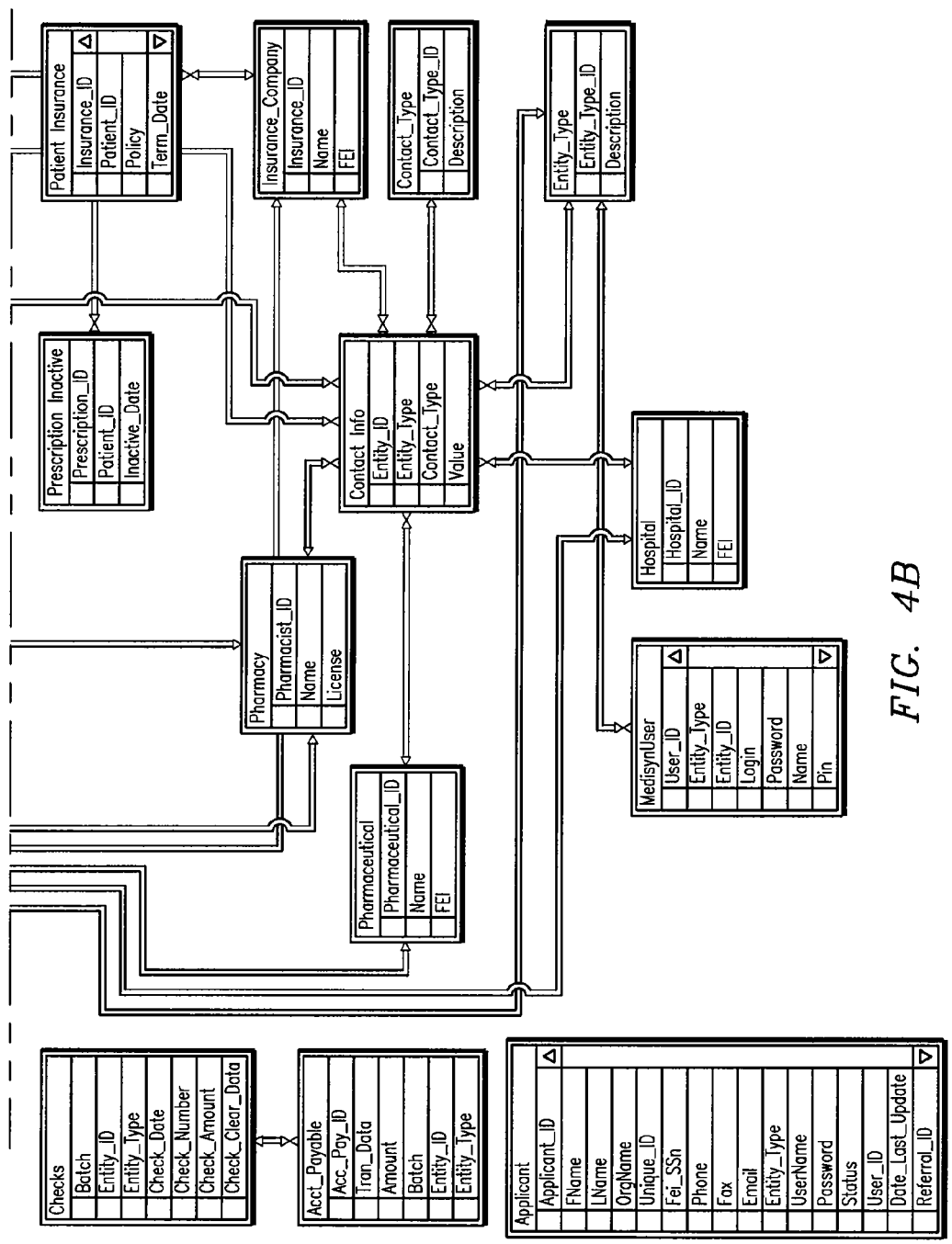

FIG. 4 illustrates an exemplary layout of a data structure 100 of a plurality of computer-readable records or pages including respective data fields for securely and accurately managing medical records of a plurality of patients. For example, respective data fields of a computer-readable page comprising data indicative of a respective physician or doctor would be Doctor_Id, First Name, Last Name, UPIN, FEI, Parent_Id and Pay Level_ID. Similarly, respective data fields of a computer-readable page comprising a progress note would be Note_Id, Patient_Id, Note_Date/Time, Doctor_Id, Note, Valid, Transcript_Id.

As shown in FIG. 4, the computer-readable progress note page may be logically interconnected to a computer-readable progress problem page and/or a progress description page. The progress problem page may be in turn connected to a computer-readable page comprising a problem list including a list of inactive problems. Similarly, the computer-readable progress prescription page may be logically interconnected to a computer-readable page comprising a prescription list including a list of inactive prescriptions. Each of the users has a respective computer-readable address page comprising data indicative of address information for each user. A computer-readable page comprising data indicative of patient information may be linked to a computer-readable page comprising patient insurance information and in turn to a page comprising insurance company data of a given patient. The type of user may be identified based on entity type. In addition, each user may have a corresponding computer-readable page comprising contact information. As suggested above, the tracking module may track system access and the type of entity gaining such access to generate billing information including payable and receivable accounts and including type of payment, such as check payment, credit card payment, etc. A computer-readable applicant page may comprise respective data fields corresponding to a prospective user of the system.

The present invention can be embodied in the form of computer-implemented processes and apparatus for practicing those processes. The present invention can also be embodied in the form of computer program code containing computer-readable instructions embodied in tangible media, such as floppy diskettes, CD-ROMs, hard drives, or any other computer-readable storage medium, wherein, when the computer program code is loaded into and executed by a computer, the computer becomes an apparatus for practicing the invention. The present invention can also be embodied in the form of computer program code, for example, whether stored in a storage medium, loaded into and/or executed by a computer, or transmitted over some transmission medium, such as over electrical wiring or cabling, through fiber optics, or via electromagnetic radiation, wherein, when the computer program code is loaded into and executed by a computer, the computer becomes an apparatus for practicing the invention. When implemented on a general-purpose computer, the computer program code segments configure the computer to create specific logic circuits or processing modules.

Appendix I comprises exemplary COM interfaces including flow diagrams which may be utilized to control operation of a system embodying the present method for managing medical records. By way of example and not of limitation, the interfaces in Appendix I were written using MS Visual Basic syntax.

It will be understood that the specific embodiment of the invention shown and described herein is exemplary only. Numerous variations, changes, substitutions and equivalents will now occur to those skilled in the art without departing from the spirit and scope of the present invention. Accordingly, it is intended that all subject matter described herein and shown in the accompanying drawings be regarded as illustrative only and not in a limiting sense and that the scope of the invention be solely determined by the appended claims.

What is claimed is:

1. A computerized method for managing respective health records of a plurality of patients, said method comprising:
   uploading a progress note of a respective patient, said progress note comprising data relative to an encounter between a respective physician and the respective patient;
   identifying on said progress note respective parameters selectable by the respective physician;
   storing said progress note with said identified parameters in a computer database accessible to a plurality of authorized users; and
   populating said computer database with respective progress notes and respective identified parameters resulting from further encounters between the respective patient and any respective physician so as to create a historical set of progress notes with identified parameters for that respective patient, the set of historical progress notes being interconnectable based on one or more logic operators.

2. The computerized method of claim 1, wherein the identified parameters are selected to convey a snapshot of said encounter.

3. The computerized method of claim 1, wherein the identified parameters are selected from the group consisting of diagnosis and prescription parameters.

4. The computerized method of claim 1, wherein one of the logical operators comprises a chronology-indicative operator.

5. The computerized method of claim 1, wherein one of the logical operators comprises a pathology-indicative operator.

6. The computerized method of claim 1, wherein one of the logical operators comprises a pharmacology-indicative operator.

7. The computerized method of claim 1 further comprising:
   tracking users accessing information in the database to process respective billing of the accessing users for each access of the database, and
   allocating fees among entities associated with the respective information accessed by respective users.

8. The computerized method of claim 1, wherein the database is accessible to a plurality of users through a communications network.

9. The computerized method of claim 8, wherein the communications network comprises the Internet.

10. The method of claim 1, further comprising controlling access of the database according to ownership interests assigned to information in the database.

11. A computer readable medium encoded with computer code for managing respective health records of a plurality of patients, the program code causing a computer to execute a method comprising:
    uploading a progress note of a respective patient, said progress note comprising data relative to an encounter between a respective physician and the respective patient;
    identifying on said progress note respective parameters selectable by the respective physician;
    storing said progress note with said identified parameters in a database accessible to a plurality of authorized users; and
    populating said database with respective progress notes and respective identified parameters resulting from further encounters between the respective patient and any respective physician so as to create a historical set of progress notes with identified parameters for that respective patient, the set of historical progress notes being interconnectable based on one or more logic operators.

12. The computer readable medium of claim 11, wherein the identified parameters are selected to convey a snapshot of said encounter.

13. The computer readable medium of claim 11, wherein the identified parameters are selected from the group consisting of diagnosis and prescription parameters.

14. The computer readable medium of claim 11, wherein one of the logical operators comprises a chronology-indicative operator.

15. The computer readable medium of claim 11, wherein one of the logical operators comprises a pathology-indicative operator.

16. The computer readable medium of claim 11, wherein one of the logical operators comprises a pharmacology-indicative operator.

17. The computer readable medium of claim 11, further comprising:
  tracking users accessing information in the database to process respective billing of the accessing users for each access of the database, and
  allocating fees among entities associated with the respective information accessed by respective users.

18. The computer readable medium of claim 11, wherein the database is accessible to a plurality of users through a communications network.

19. The computer readable medium of claim 18, wherein the communications network comprises the Internet.

* * * * *